US00PP17724P3

(12) United States Plant Patent
Abrahamson et al.

(10) Patent No.: US PP17,724 P3
(45) Date of Patent: May 15, 2007

(54) FAST-GROWING WILLOW SHRUB NAMED 'CANASTOTA'

(50) Latin Name: ***Salix sachalinensis*×*S. miyabeana***
Varietal Denomination: Canastota

(75) Inventors: Lawrence P. Abrahamson, Marcellus, NY (US); Richard F. Kopp, Marietta, NY (US); Lawrence B. Smart, Geneva, NY (US); Timothy A. Volk, Syracuse, NY (US)

(73) Assignee: The Research Foundation of State Univsersity of New York, Albany, NY (US)

( * ) Notice: Subject to any disclaimer, the term of this patent is extended or adjusted under 35 U.S.C. 154(b) by 0 days.

(21) Appl. No.: 11/244,986

(22) Filed: Oct. 6, 2005

(65) Prior Publication Data

US 2007/0083962 P1 Apr. 12, 2007

(51) Int. Cl.
*A01H 5/00* (2006.01)

(52) U.S. Cl. ..... Plt./216

(58) Field of Classification Search ..... Plt./216
See application file for complete search history.

*Primary Examiner*—Kent Bell
(74) *Attorney, Agent, or Firm*—Wall Marjama & Bilinski LLP

(57) ABSTRACT

A distinct male cultivar of *Salix sachalinensis*×*S. miyabeana* named 'Canastota', characterized by rapid stem growth producing greater than 2.7-fold more woody biomass than its female parent (*Salix sachalinensis* 'SX61'), 28% greater woody biomass yield than its male parent (Salix miyabeana 'SX64'), and 20% greater woody biomass yield than a standard production cultivar, *Salix dasyclados* 'SV1' when grown in the same field for the same length of time (two growing seasons after coppice) in Tully, N.Y. 'Canastota' can be planted from dormant stem cuttings, produces multiple stems after coppice, and the stem biomass can be harvested when the plant is dormant. In the spring following harvest, the plant will re-sprout very vigorously, producing new stems that can be harvested after two to four years of growth. This harvest cycle can be repeated several times. 'Canastota' displays a low incidence of rust disease or damage by willow sawfly.

11 Drawing Sheets

STATEMENT AS TO RIGHTS TO INVENTIONS MADE UNDER FEDERALLY-SPONSORED RESEARCH AND DEVELOPMENT

The invention described herein was reduced to practice during the funding period of Contract 4000003235 (SUNY Research Foundation Award 011275) awarded by Oak Ridge National Laboratory, managed by UT-Batelle for the United States Department of Energy under contract DE-AC05-00OR22725, and of agreement number 6267 (SUNY Research Foundation Award 011536) awarded by the New York State Energy Research and Development Authority.

CROSS-REFERENCE TO RELATED APPLICATIONS

This application is related to the following plant patent applications, all of which are subject to assignment to the Research Foundation of the State University of New York, and each of which is being filed on even date herewith: "Fast-Growing Shrub Willow" Named 'Fish Creek', application Ser. No. 11/244,988; "Fast-Growing Shrub Willow" Named 'Millbrook', application Ser. No. 11/244,636; "Fast-Growing Shrub Willow" Named 'Oneida', application Ser. No. 11/244,975; "Fast-Growing Shrub Willow" Named 'Otisco', application Ser. No. 11/244,987; "Fast-Growing Shrub Willow" Named 'Owasco', application Ser. No. 11/244,842; and "Fast-Growing Shrub Willow" Named 'Tully Champion', application Ser. No. 11/244,635. The variety of fast-growing shrub willow named 'Canastota' was produced in the willow breeding program at the State University of New York College of Environmental Science and Forestry, as were other varieties, including: 'Fish Creek', 'Millbrook', 'Oneida', 'Otisco', 'Owasco', and 'Tully Champion'.

BACKGROUND OF THE INVENTION

1. Field of the Invention

The invention is a new and distinct cultivar known by the varietal name 'Canastota' resulting from the novel hybridization of *Salix sachalinensis* with *Salix miyabeana*. The new variety was produced through controlled willow breeding conducted by the inventors at the State University of New York College of Environmental Science and Forestry in Syracuse, N.Y. The objective of the breeding program is to produce new willow cultivars that generate high biomass yields on a variety of sites, are resistant to diseases and pests, and possess agronomic traits suitable for mechanical planting, harvesting, and post-harvest processing. Shrub willow being developed as an agricultural crop plant that will be grown and harvested as a sustainable, renewable source of energy. Once a field planting of shrub willows is established, the woody stems can be harvested every three years, and new shoots will re-sprout the following season. Repeated harvesting every two to four years can be sustained for at least 15 years.

2. Description of Relevant Prior Art Including Information Disclosed Under 37 CFR 1.97–1.99

This new variety of *Salix sachalinensis*×*S. miyabeana* was the seedling progeny of the controlled pollination of the female clone *Salix sachalinensis* 'SX61' by the male cone *Salix miyabeana* 'SX64' performed in February 1999 in Syracuse, N.Y. The new variety is distinguished from the female parent in that it is male. The plant has been propagated repeatedly by stem cuttings and has been found to retain its distinctive characteristics through successive propagations and field trials. More specifically, the plant has been asexually reproduced by collecting dormant stems during the winter months from a plant growing in Syracuse, N.Y.; cutting them into 5 inch or 10 inch pieces (cuttings); then planting those cuttings in the field in Tully, N.Y. in the spring or in potting mix in the greenhouse, then transplanting the rooted cuttings to the field in Tully, N.Y.

Both parents (*Salix sachalinensis* 'SX61' and *Salix miyabeana* 'SX64') were originally transferred from Toronto, Ontario, Canada, to Syracuse, N.Y. in 1994 and were vegetatively propagated from stem cuttings. The growth of the parent plants was characterized in experimental studies in Tully, N.Y. Both parents displayed rapid stem growth and low incidence of rust disease, so were chosen to serve as parents in a cross. The seedlings produced by this cross (cross identification # 9970) were first established in a greenhouse, and then were transplanted to a field in Syracuse, N.Y. This particular individual (individual #9970-036) was selected from the family due to its exceptional stem height growth.

The new cultivar has been grown in Syracuse, N.Y. and Tully, N.Y., which have a normal yearly average daily temperature of 47° F., normal daily maximum temperature in July of 82° F., normal daily minimum temperature in January of 14° F., and average precipitation of 40 inches. The new cultivar grows from a rooted cutting to a fully mature plant ready for harvest in approximately three years.

SUMMARY OF THE INVENTION

The *Salix sachalinensis*×*S. miyabeana* cultivar 'Canastota' has not been observed under all possible environmental conditions. The phenotype may vary somewhat with variations in environments such as temperature, light intensity and length of illumination, without, however, any variation in genotype. The new and distinct cultivar presents the following traits that have been repeatedly observed and are determined to be the unique characteristics of 'Canastota'. These characteristics in combination distinguish 'Canastota' as a new and distinct cultivar:

1. Rapid growth rate, producing greater than 2.7-fold more woody biomass than its female parent (*Salix sachalinensis* 'SX61'), 28% greater woody biomass yield than its male parent (*Salix miyabeana* 'SX64'), and 20% greater woody biomass yield than a standard production cultivar, *Salix dasyclados* 'SV1' when grown in the same field for the same length of time (two growing seasons after coppice) in Tully, N.Y.
2. Low incidence of rust disease or willow sawfly damage as assessed in nursery plantings in Tully, N.Y. in October, 2004.

BRIEF DESCRIPTION OF THE DRAWING

The accompanying color photographs show the features of the claimed cultivar in a manner as true as is reasonably possible. The illustrations include:

FIG. 1.1 illustrates two-year-old portion of stem collected while dormant;

FIG. 1.2 illustrates one-year-old portion of stem collected while dormant;

FIG. 1.3 illustrates a vegetative bud in dormancy;

FIG. 1.4 illustrates a floral bud in dormancy;

FIG. 1.5 illustrates new shoot growth from a stem cutting rooted in soil:sand in a greenhouse;

FIG. 1.6 illustrates upper leaf surface;

FIG. 1.7 illustrates lower leaf surface;

FIG. 1.8 illustrates mature catkin;

FIG. 1.9 illustrates stamen and densely pubescent floral bract;

FIG. 1.10 illustrates lenticels; and

FIG. 2.1 illustrates the biomass yield two years after coppice in Tully, N.Y. as compared to other shrub willows.

DETAILED DESCRIPTION OF THE NEW PLANT

The following detailed description sets forth characteristics of the new plant. The following observations and measurements describe plants grown by asexual reproduction in Syracuse, N.Y. or Tully, N.Y. under conditions as described hereinabove. Color references are made using The Royal Horticultural Society Colour Chart (hereinafter The R.H.S. Colour Chart) of The Royal Horticultural Society of London, England, except where general terms of ordinary dictionary significance are used.

BOTANICAL DESCRIPTION OF THE PLANT

The following detailed description of the 'Canastota' variety is based on observations from 10 inch cuttings grown in a greenhouse in Syracuse, N.Y. Cuttings were grown in 7 inch tubes in a (1:1) ProMix®/sand (v/v) substrate under natural light from December 2004 to March 2005. Plants were irrigated with automatic misting for 6 minutes at 2 hour intervals five times each day.

Latin name: *Salix sachalinensis*×*S. miyabeana.*
Varietal denomination: 'Canastota'.
Parentage:
*Female or seed parent.*—*S. sachalinensis* 'SX61'.
*Male or pollen parent.*—*S. miyabeana* 'SX64'.
Propagation:
*Type.*—Stem cuttings.
*Time to rooting.*—Approximately 10 days in water at 21° C.
Precocity: Subprecocious — Catkins mature as leaves begin to break bud.
Plant description: The color of one-year-old stems observed when dormant is typically grey orange (RHS 171A), while two-year-old stems are yellow-green (RHS 152B) with bark beginning to crack and the cuticle broken and textured. Dormant vegetative buds are dark red (RHS 180A), 4.5 mm in length, narrow, and acute. Lenticels are peach colored and randomly scattered, 0.5–1 mm in diameter. The leaves are simple and alternate with pinnate venation. The upper surface of leaves is glabrous and glossy with distinct pinnate venation. The lower surface is glabrous and slightly glaucous. Typical petioles on mature leaves grown under field conditions in early October are 4 mm in length, green-yellow (#1B) and 1.5–2.0 mm in diameter. The petiole in FIGS. 1.6–1.7 from a greenhouse-grown plant is green (144D) and 1 mm wide. Stipules are lanceolate, serrate, curved, and typically 3–4 mm in length. Pubescent immature leaves. Mature leaves are oblong, acute apex, acute to obtuse base, typically 8.5–12.0 cm in length, 1.7–2.1 cm in width, serrate margin, adaxial (upper) surface green (RHS 144A), abaxial (lower) surface pale green (RHS 143C), and stem light pale green (RHS 144D) at 5 weeks of growth. The typical diameter of two-year old stems at a height of 1 m is 1.5 cm. The bark color of field-grown stems determined in early October after two growing seasons is greyed-green (#195A). The surface is slightly textured with shallow thin longitudinal furrows and raised reddish lenticels. The average plant height of a mature plant after three seasons of growth is 5–6 m, with a typical spread at the crown of 1.0–1.5 m in the typical planting spacing of 0.6 m×0.7 m.

Flowering description: Dormant floral buds are ovate, diameter rounded, beak-like apex, slightly raised to form a very small acute angle with stem, typically 10 mm in length, bright dark red (RHS 60A). Peduncle of catkin is short and bears four leafy bracts. Catkins are curved 90–180°, typically 2.8 cm in length, broadly cylindrical, and densely flowered. Flowers have one stamen, and one nectary, a densely pubescent floral bract with a green base and pink-purple obtuse apex, long united filament two times the length of the floral bract, and small anthers.

Field growth characteristics: Determined through surveys of plants growing in the field in Tully, N.Y.

Disease and pest resistance: Surveys completed in October 2004 in Tully, N.Y. indicate no to low levels of detectable rust incidence and no to low incidence of sawfly or beetle damage.

Temperature tolerance: Stems typically do not suffer frost damage at temperatures as low as 10° F. and may suffer only minor tip dieback at lower temperatures.

Seed production: None — does not produce female flowers.

Biomass yield: Mean total dry stem biomass expressed as oven dry tons (odt) per hectare (ha) and year (yr) produced through two growing seasons after coppice in four 4-plant plots ('Canastota', 13.3 odt $ha^{-1}$ $yr^{-1}$) measured in a yield trial growing in Tully, N.Y. in February 2005 was greater than the mean biomass yield of either parent ('SX61', 4.8 odt $ha^{-1}$ $yr^{-1}$; 'SX64', 10.4 odt $ha^{-1}$ $yr^{-1}$) and was greater than a current production cultivar ('SV1', 11.0 odt $ha^{-1}$ $yr^{-1}$) growing in the same trial (FIG. 2.1).

What is claimed is:

1. A new and distinct variety of a *Salix sachalinensis*×*S. miyabeana* plant substantially as illustrated and described herein.

* * * * *

Fig. 1.1
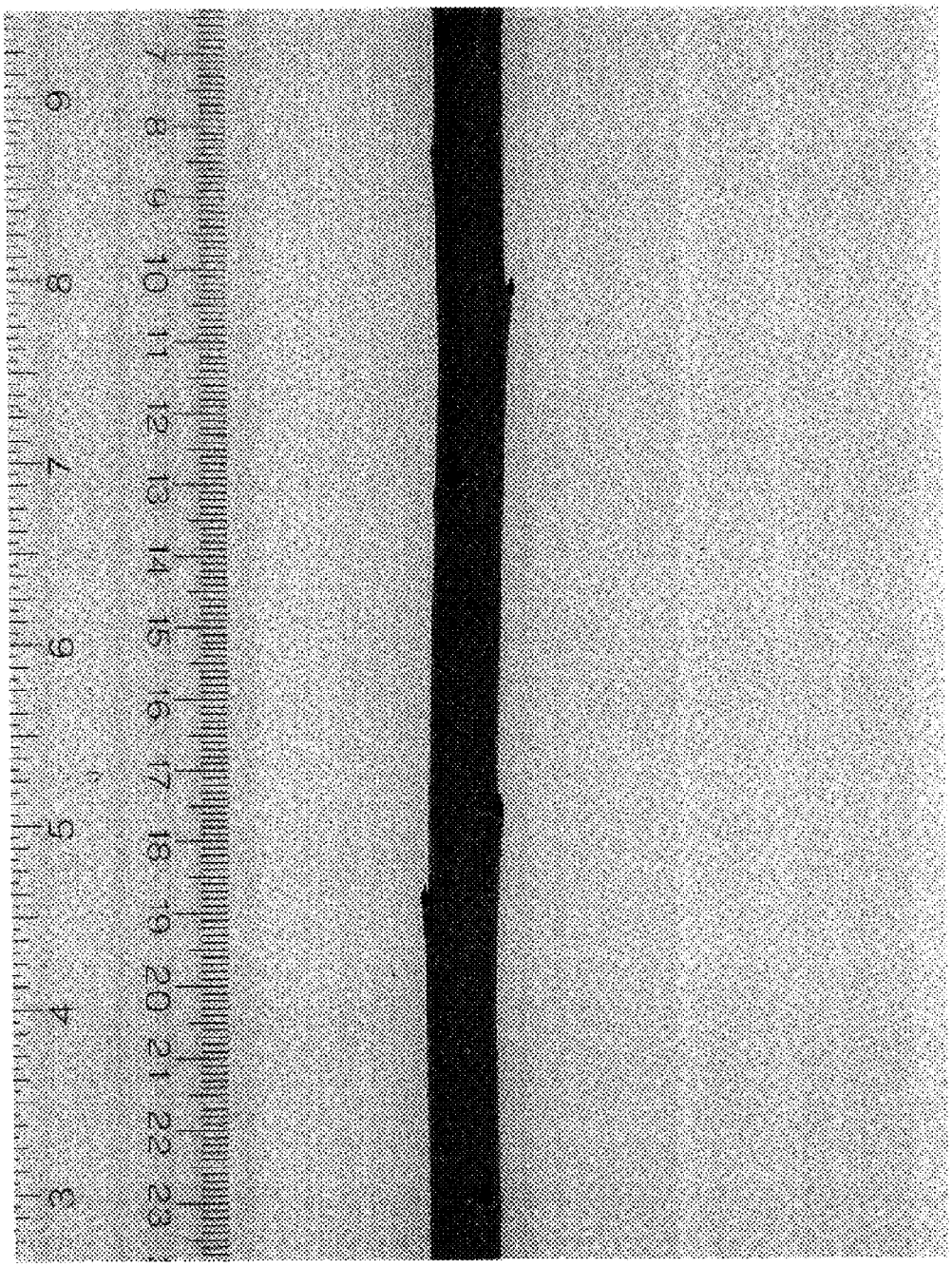

Fig. 1.2
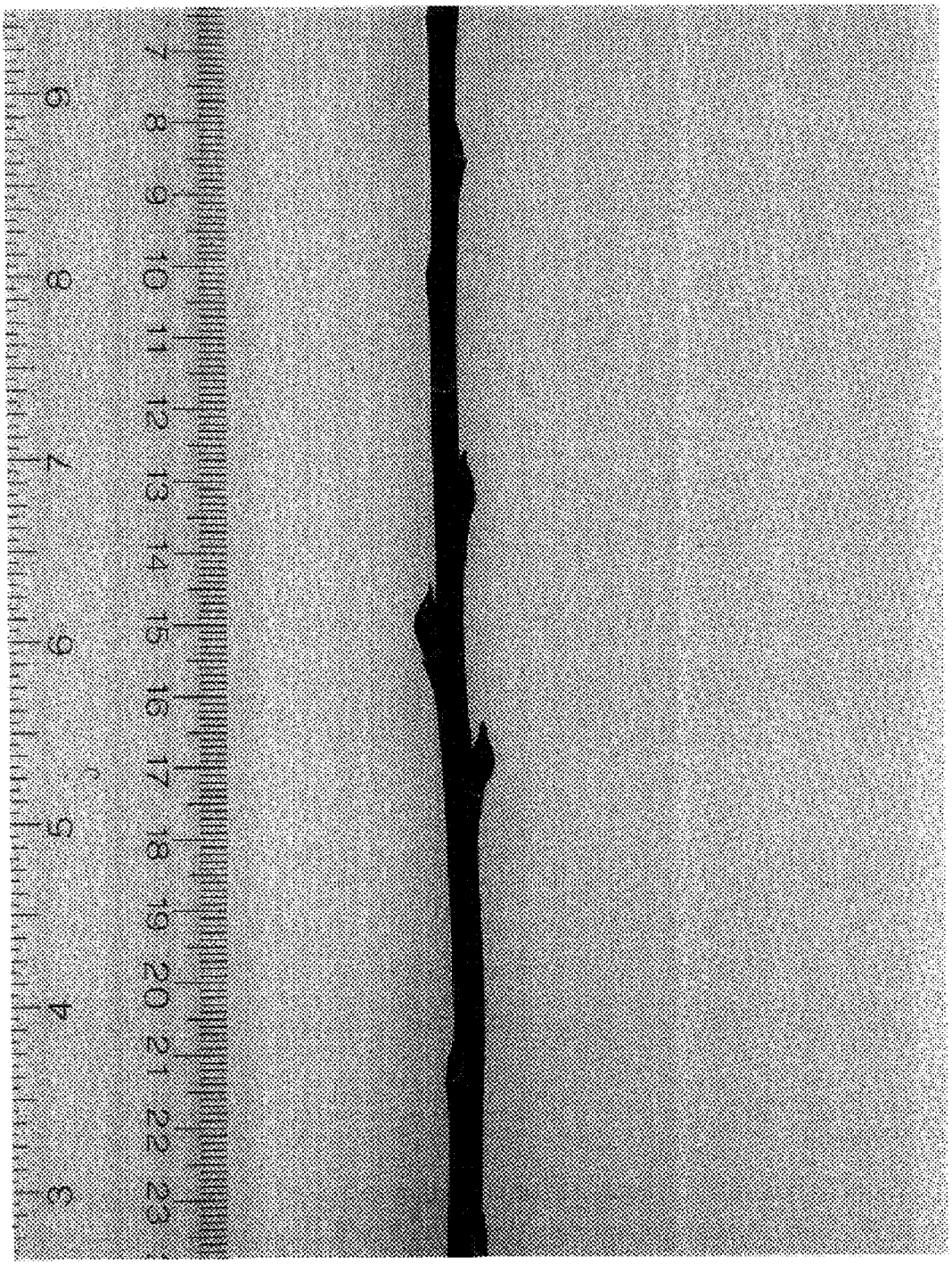

Fig. 1.3
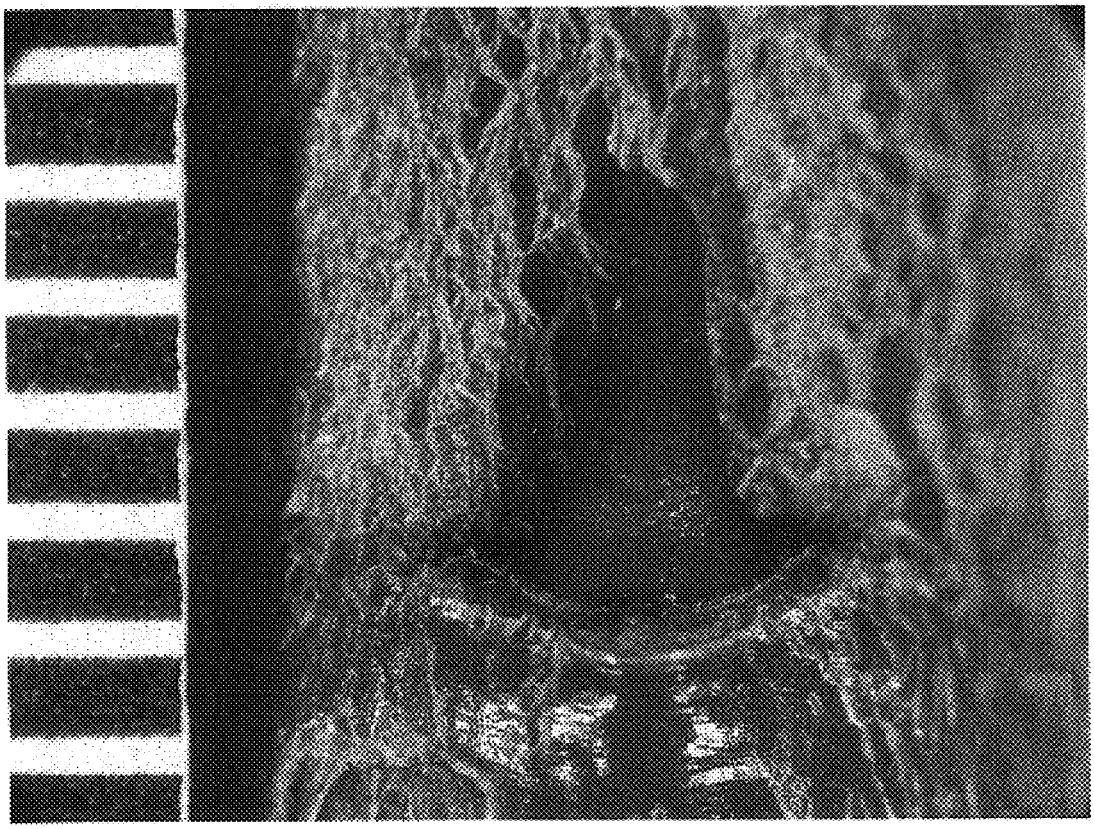

Fig. 1.4
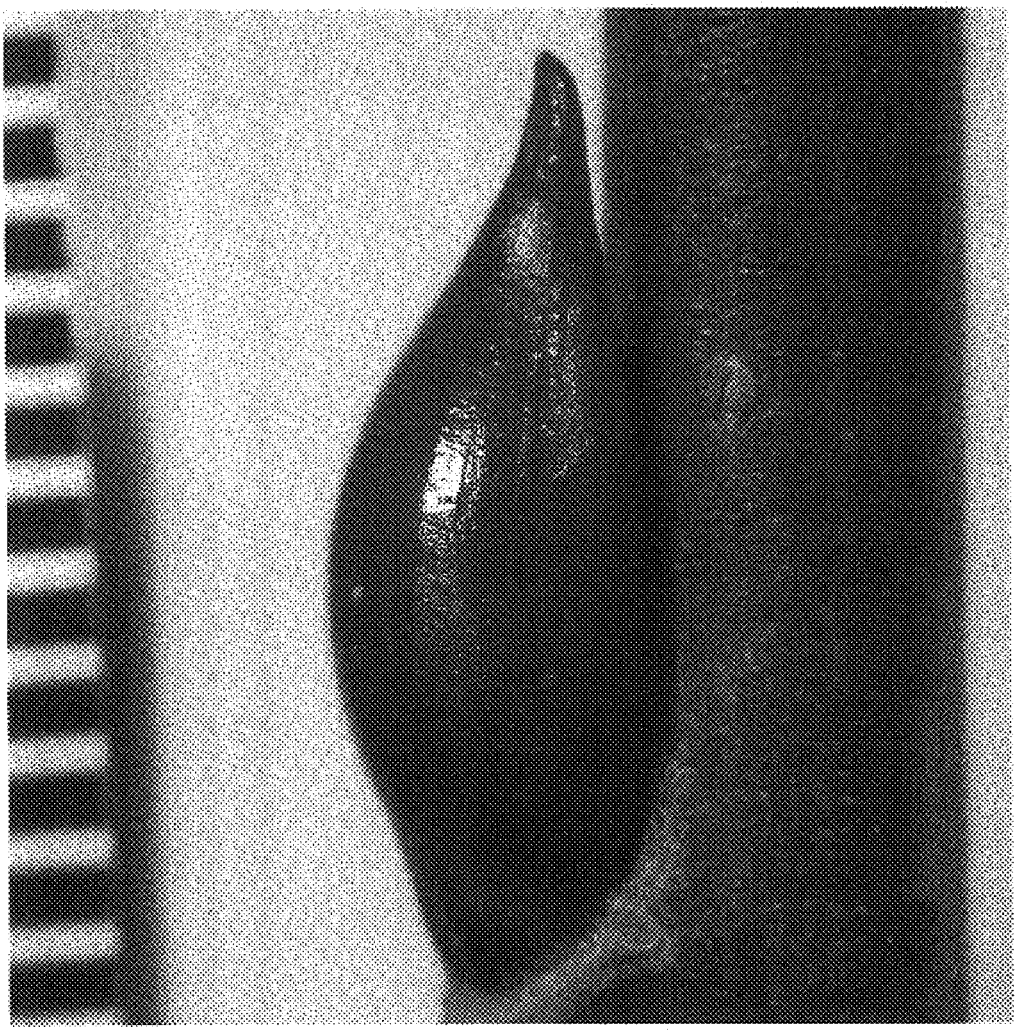

Fig. 1.5
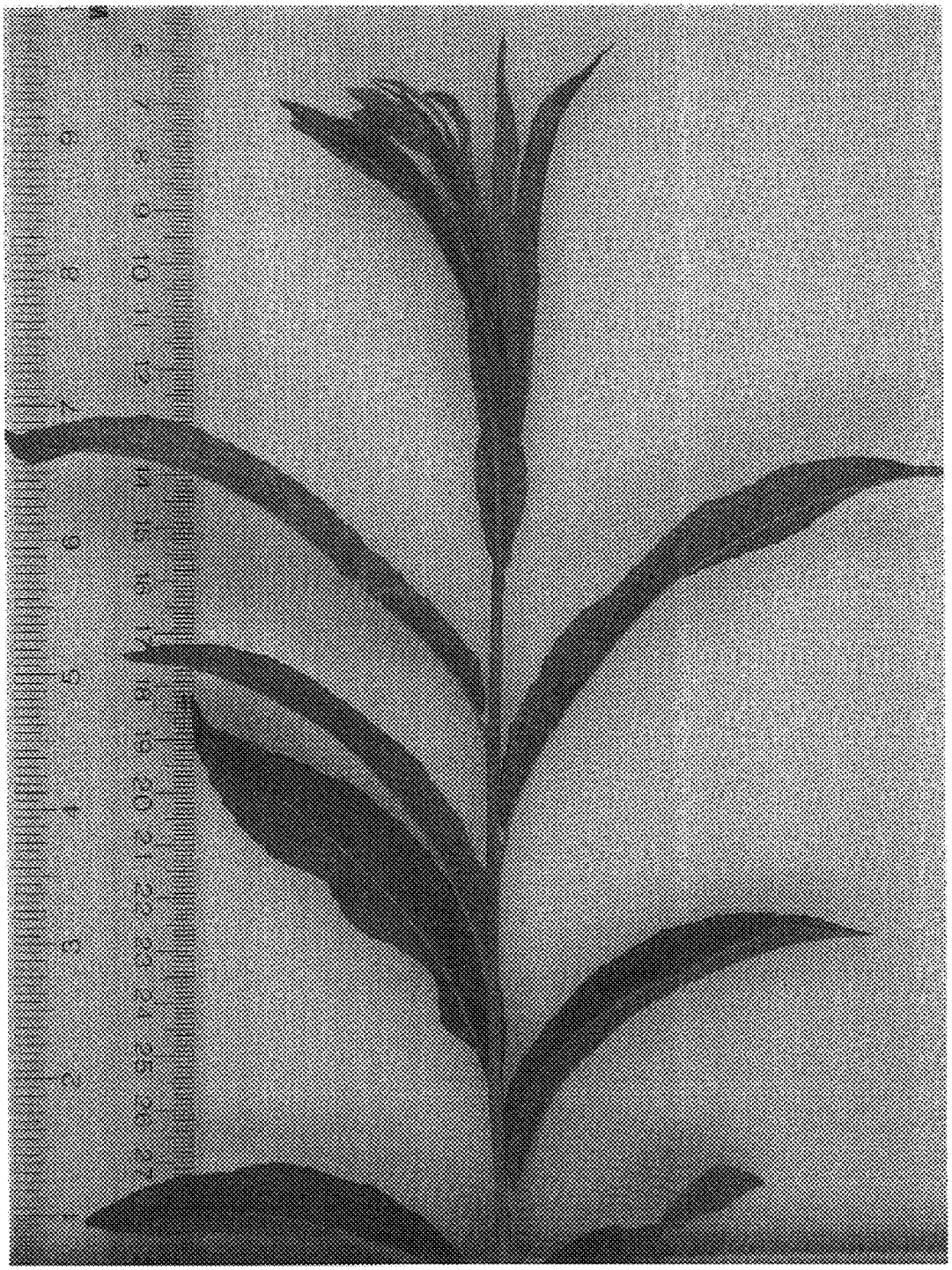

Fig. 1.6
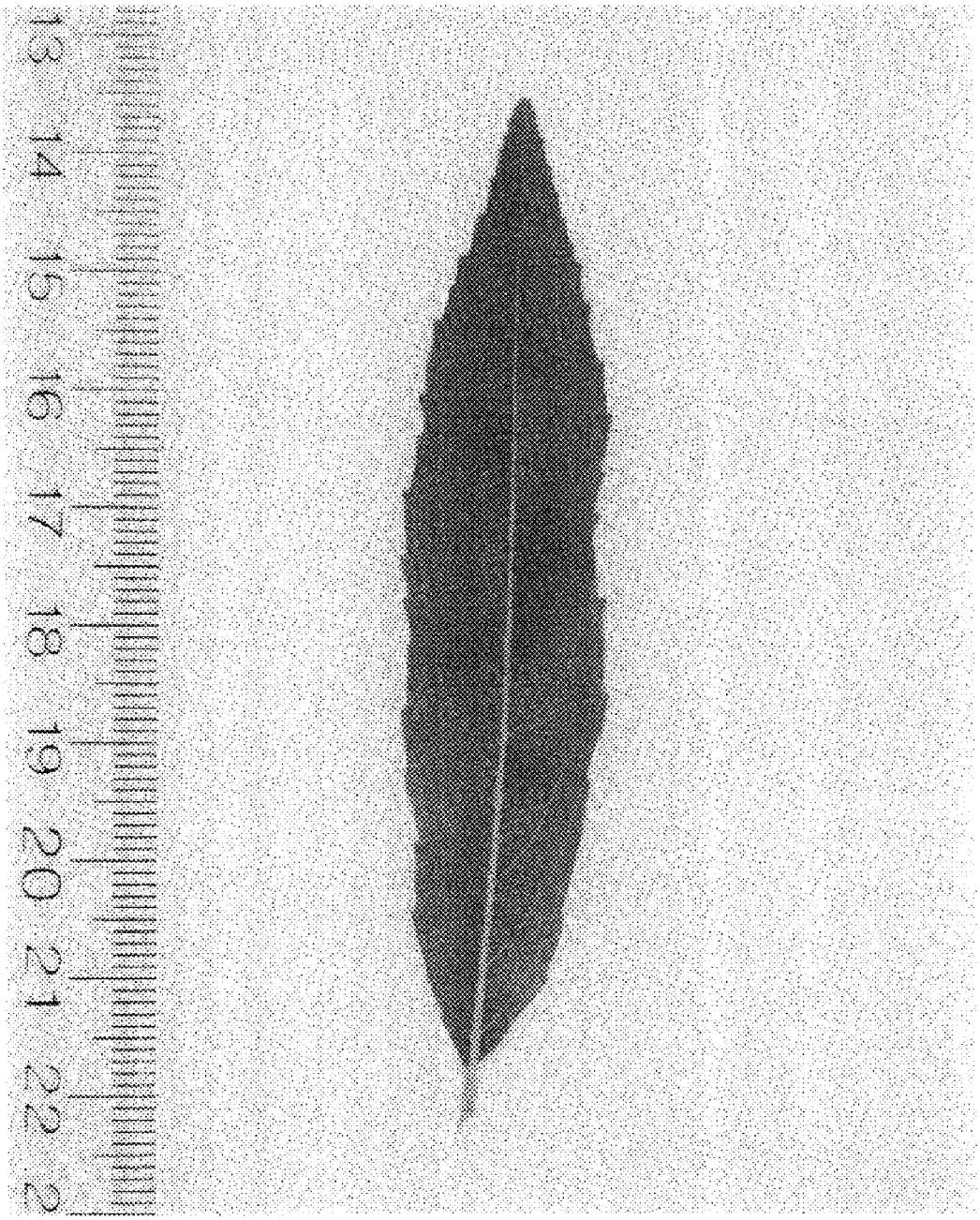

Fig. 1.7
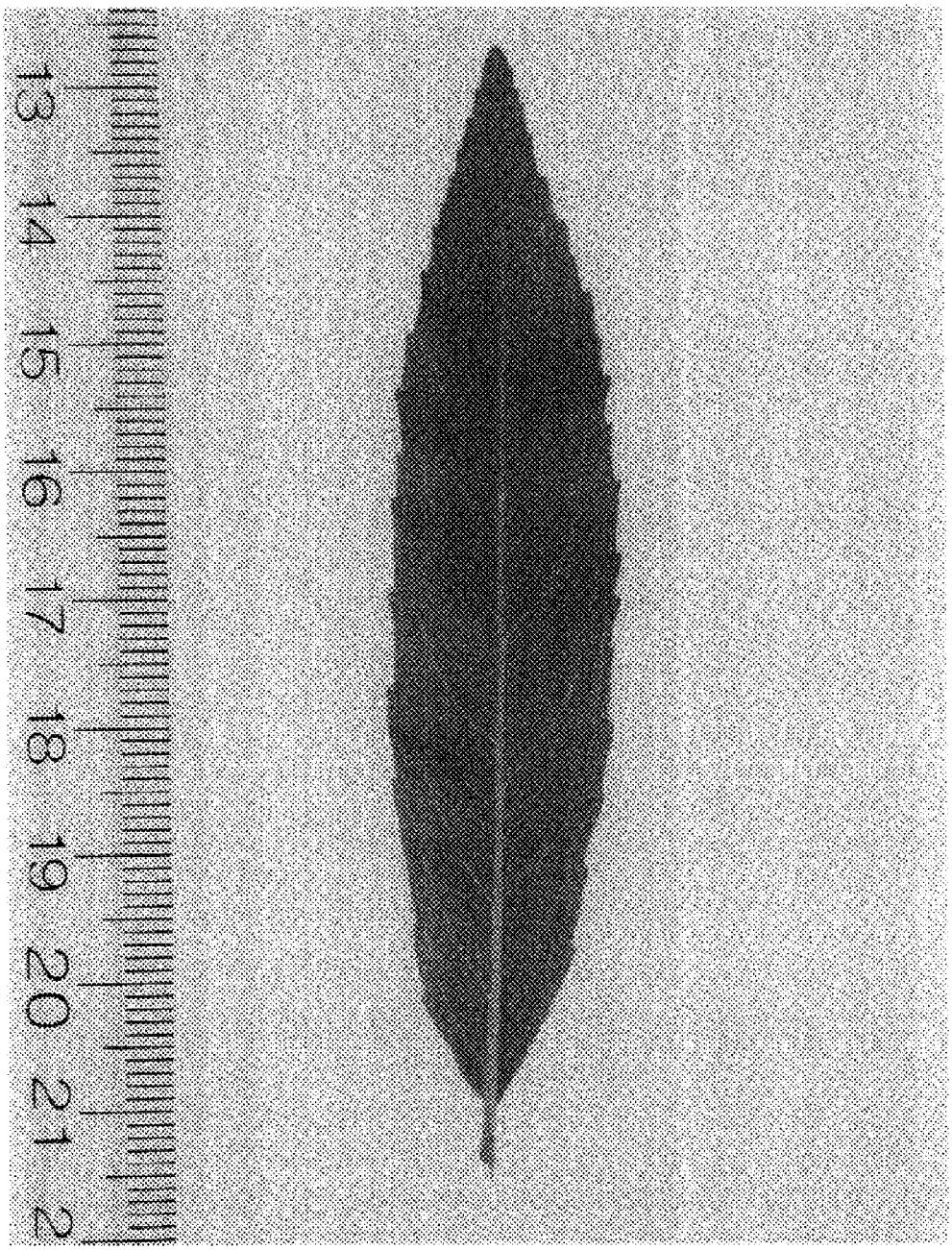

Fig. 1.8
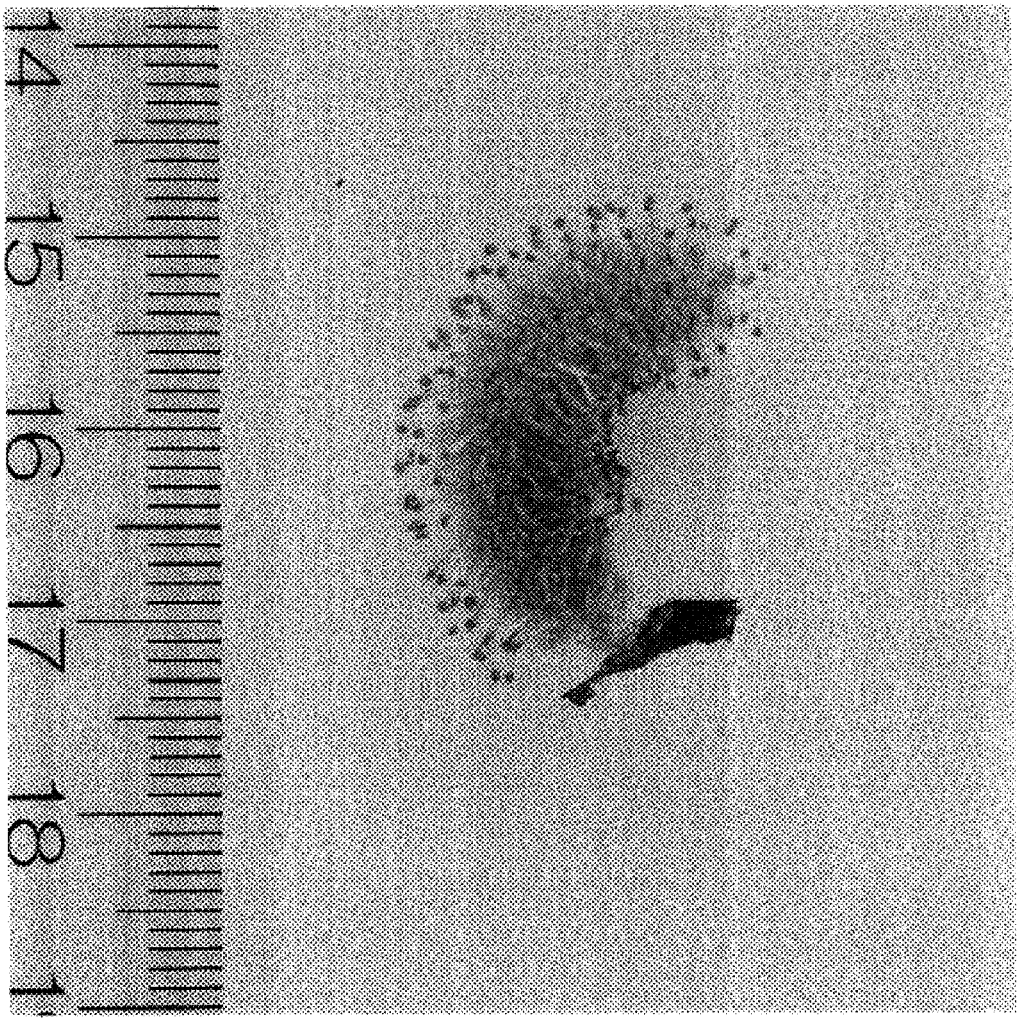

Fig. 1.9
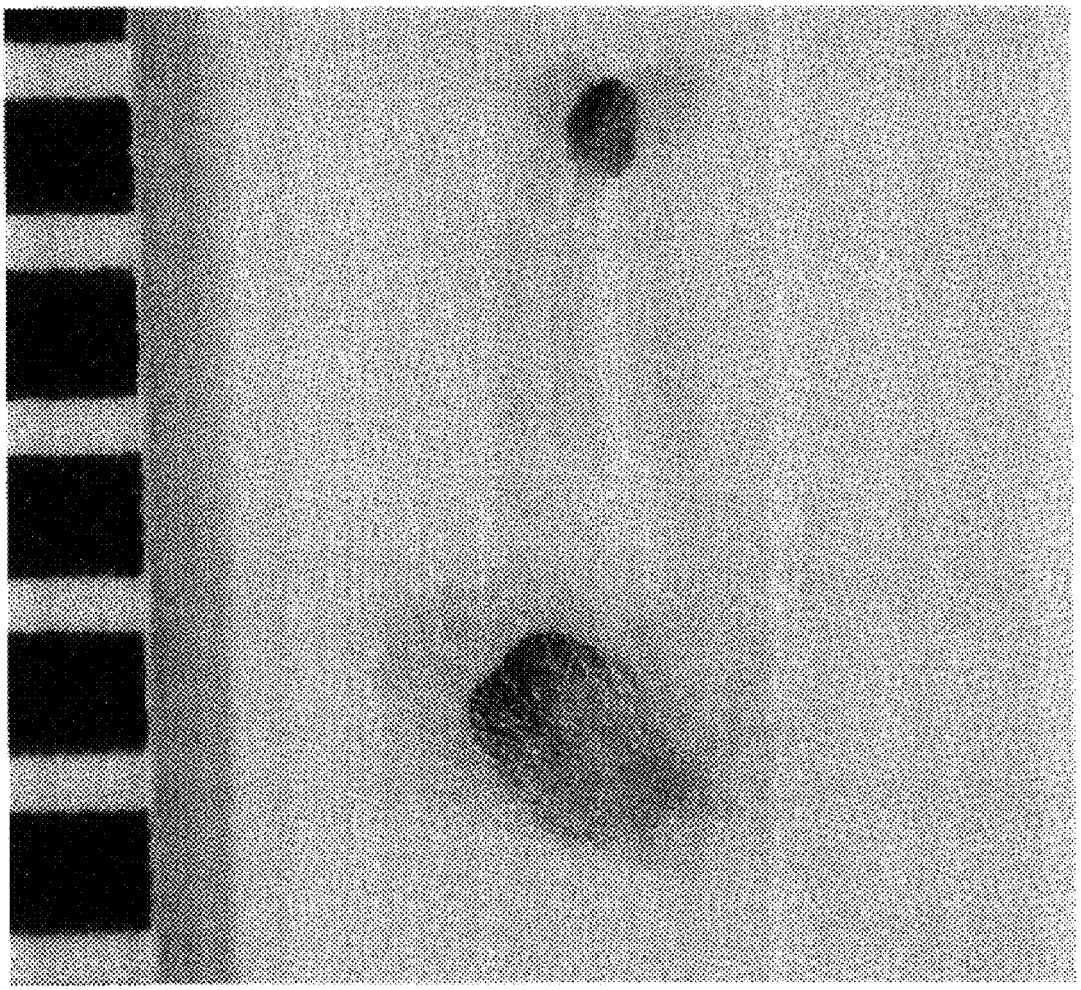

Fig. 1.10
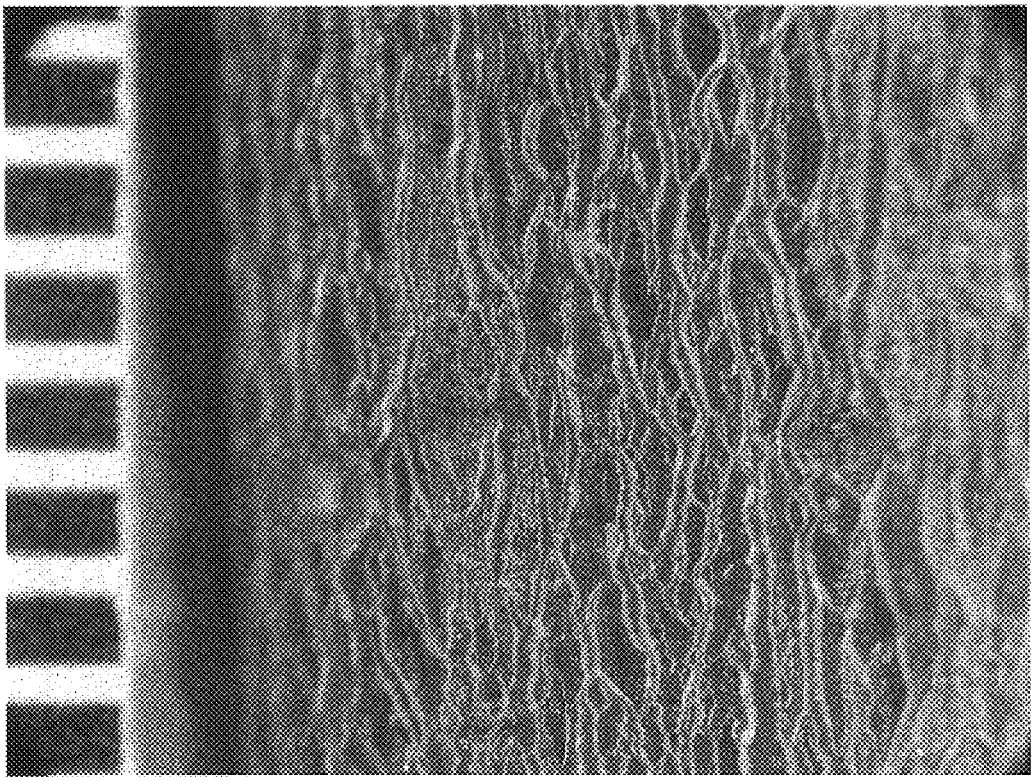

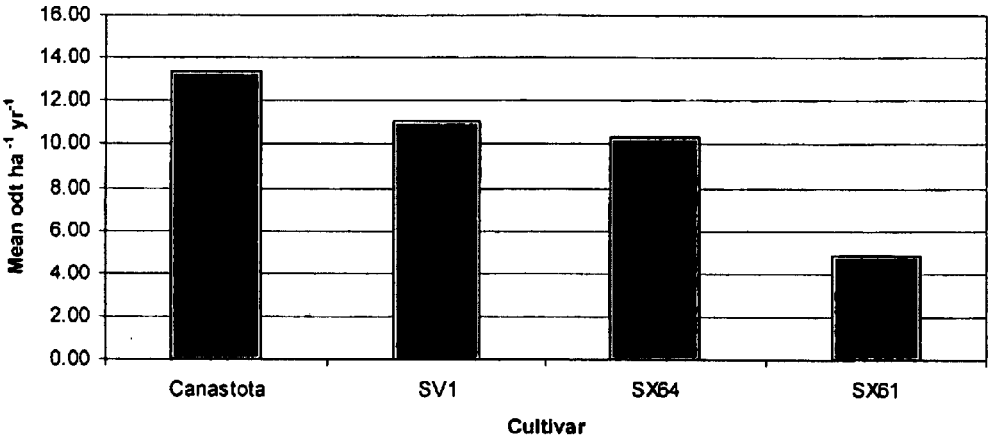

Fig. 2.1 - Biomass yield two years after coppice - Tully, NY